United States Patent [19]
Bretton

[11] Patent Number: 5,445,637
[45] Date of Patent: Aug. 29, 1995

[54] METHOD AND APPARATUS FOR PREVENTING POSTERIOR CAPSULAR OPACIFICATION

[75] Inventor: Randolph H. Bretton, Maryland Heights, Mo.

[73] Assignee: American Cyanamid Company, Wayne, N.J.

[21] Appl. No.: 301,465

[22] Filed: Sep. 7, 1994

Related U.S. Application Data

[63] Continuation-in-part of Ser. No. 162,688, Dec. 6, 1993.

[51] Int. Cl.6 .................. A61B 17/20; A61B 17/28
[52] U.S. Cl. ........................................ 606/41; 606/6; 606/107; 604/22
[58] Field of Search ............... 606/4, 5, 6, 107, 41, 606/42; 604/22

[56] References Cited

U.S. PATENT DOCUMENTS

| | | | |
|---|---|---|---|
| 4,562,600 | 1/1986 | Ginsberg et al. | 623/6 |
| 4,694,828 | 9/1987 | Eichenbaum | 606/6 |
| 4,960,418 | 10/1990 | Tennant | 606/107 |
| 5,112,328 | 5/1992 | Taboada et al. | 606/4 |
| 5,118,590 | 6/1992 | Dubroff | 604/22 |
| 5,123,902 | 6/1992 | Muller et al. | 606/5 |
| 5,209,776 | 5/1993 | Bass et al. | 606/214 |

Primary Examiner—Stephen C. Pellegrino
Assistant Examiner—Sonya C. Harris
Attorney, Agent, or Firm—Brian R. Woodworth; David A. Warmbold

[57] ABSTRACT

A method and apparatus for destroying residual lens epithelial cells. The apparatus includes a probe configured for insertion into the eye between the iris and the lens capsule. The probe is further configured to deliver energy therefrom to residual lens epithelial cells within the lens capsule in order to destroy them. The method includes the steps of inserting a probe constructed in accordance with the apparatus of present invention into the eye such that a distal end portion of the probe is disposed between the iris and the lens capsule, delivering energy to the probe such that residual lens epithelial cells within the lens capsule are destroyed, ceasing the delivery of energy to the probe, and removing the probe from the eye.

14 Claims, 5 Drawing Sheets

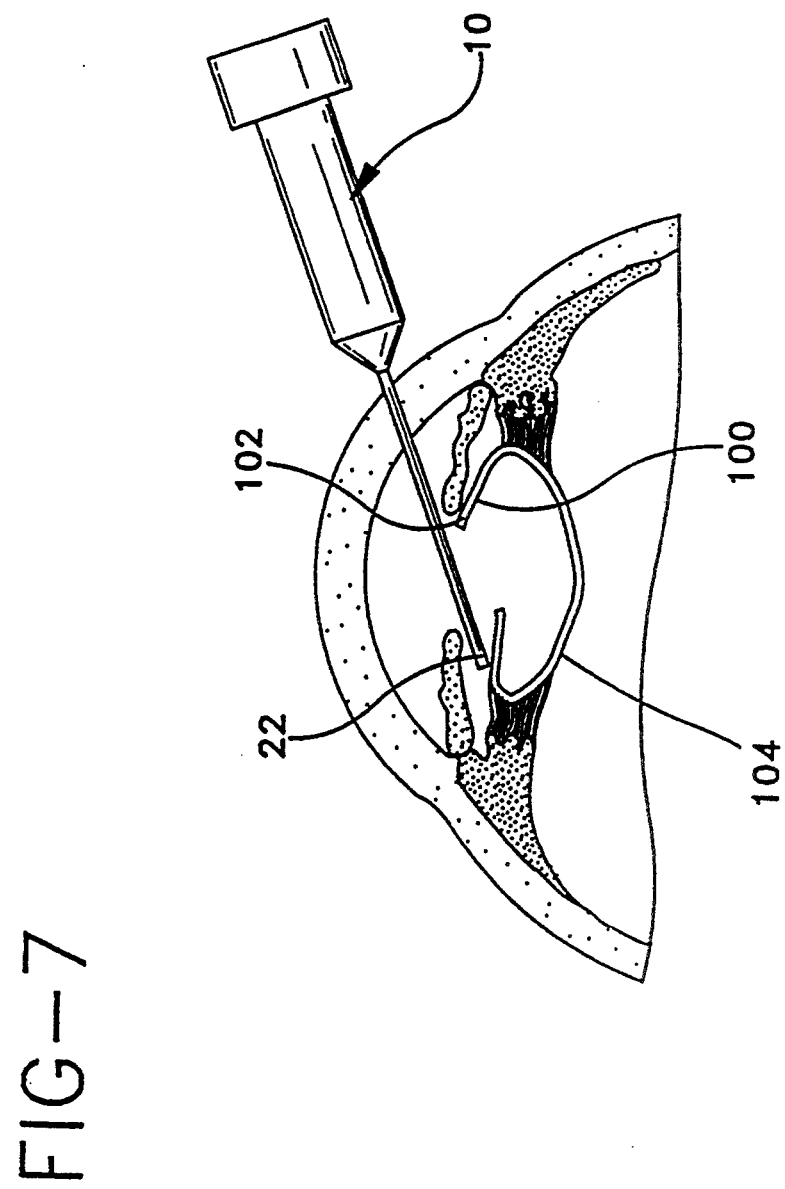

METHOD AND APPARATUS FOR PREVENTING POSTERIOR CAPSULAR OPACIFICATION

This is a continuation-in-part of U.S. Ser. No. 08/162,688 filed Dec. 6, 1993.

BACKGROUND OF THE INVENTION

The present invention relates to a method for preventing the occurrence of posterior capsular opacification (PCO) or secondary cataract formation following the extracapsular extraction of a cataractous lens. More particularly, the present invention is directed to a method for preventing the occurrence of PCO by destroying residual lens epithelial cells on the interior surface of the lens capsule of the eye through the application of energy thereto. In addition, the present invention is directed to a device configured to deliver energy to residual lens epithelial cells on the lens capsule of the eye in accordance with the method of the present invention.

Cataract extraction is among the most commonly performed operations in the United States and the world. The cataractous lens is located within a capsular sac or lens capsule which is positioned within the posterior chamber of the eye. In order to gain access to the cataractous lens, an incision is made at the limbus of the eye for the purpose of introducing a surgical instrument into the anterior chamber of the eye. In the case of extracapsular cataract extraction, a capsularhexis procedure is performed in which a portion of the anterior membrane of the lens capsule adjacent to the iris is removed using a surgical cutting instrument in order to provide direct access to the cataractous lens from the anterior chamber. The lens is then removed through various known methods, including phacoemulsification which entails the application of ultrasonic energy to the lens in order to break it into small pieces which can be aspirated from the lens capsule. With the exception of the portion of the anterior membrane of the lens capsule that is removed in order to gain access to the cataractous lens, the lens capsule remains substantially intact throughout an extracapsular cataract extraction. Following removal of the cataractous lens, an artificial intraocular lens typically is implanted within the lens capsule in order to mimic the refractive function of the original lens.

Although cataractous lens removal and intraocular lens implantation provide significant benefits to most cataract patients, it is estimated that up to fifty percent (50%) of all patients who have intraocular lenses implanted within the lens capsule will develop Posterior Capsular Opacification ("PCO") or secondary cataracts within five years after surgery. PCO is caused by the deposit of cells and fibers on the intraocular lens and on the posterior capsular membrane, thereby obstructing light passing through the intraocular lens and obscuring the patient's vision. These cell deposits originate from two sources: (1) the proliferation of residual lens epithelial cells after surgery; and (2) the accumulation of inflammatory cells and protein deposits on the intraocular lens. Of these two sources, the major cause of PCO by far is the proliferation and migration of the residual lens epithelial cells on the capsular membrane.

Ophthalmic surgeons, aware of the problems associated with residual lens epithelial cells, typically take considerable care in trying to remove all residual lens epithelial cells prior to implantation of the artificial intraocular lens. However, despite these efforts, a significant number of lens epithelial cells usually are left on the interior surface of the lens capsule due to the fact that these cells are difficult to identify and are often difficult to reach due to their position on the inside surface of the lens capsule.

The most common treatment for PCO entails the application of laser energy to the posterior membrane of the lens capsule for the purpose of destroying the lens epithelial cells propagating thereon. However, the laser energy applied to the posterior membrane of the lens capsule is ordinarily directed through the implanted intraocular lens, possibly resulting in damage to the optical and/or structural characteristics of the intraocular lens. The application of laser energy to the posterior membrane of the lens capsule also typically results in the destruction of a portion of the lens capsule as well as the residual lens epithelial cells propagating thereon. The destruction of a portion of the lens capsule creates a risk of exposure to the vitreous, possibly resulting in serious or irreparable damage to the eye. In addition, the destruction of a portion of the lens capsule creates a risk of shrinkage of the lens capsule, possibly resulting in a compromising of the optical characteristics of the intraocular lens. In certain cases, the destroyed posterior capsular tissue may regrow, e.g., as a result of a fibrin clot, thereby creating a renewed possibility of PCO. Accordingly, it is preferable to prevent the occurrence of PCO rather than attempting to treat it.

Various procedures for the prevention of PCO have been suggested in recent years. Many of these procedures have included the application of chemicals to the interior surface of the lens capsule in order to destroy residual lens epithelial cells. However, none of these procedures has proven to be particularly successful in the prevention of PCO due to the fact that it is extremely difficult to destroy residual lens epithelial cells without simultaneously destroying other cells within the eye, including the possible destruction of the corneal endothelium. Selective destruction of residual lens epithelial cells thus appears to be the key to the prevention of PCO.

SUMMARY OF THE INVENTION

The method of the present invention is directed to the application of energy to the interior surface of the lens capsule following extracapsular cataract extraction for the purpose of preventing the occurrence of PCO through the destruction of residual lens epithelial cells. In one embodiment of the method of the present invention, a surgical probe having a capacity to emit energy therefrom in a directionally controlled manner is inserted into the eye following extracapsular cataract extraction such that the distal end portion of the probe is anterior to the anterior membrane of the lens capsule. Energy is then directed to the probe such that energy is emitted therefrom in a predetermined direction through the anterior membrane of the lens capsule in order to destroy residual lens epithelial cells disposed on the interior surface of the lens capsule. The surgical probe can be moved in order to ensure that energy is delivered to substantially all portions of the lens capsule, thereby destroying as many residual lens epithelial cells as possible. The surgical probe is then deactivated and removed from the eye when the surgeon is satisfied that the requisite residual lens epithelial cells have been destroyed through the application of energy from the surgical probe. This embodiment of the present invention can be practiced either before or after extracapsular cataract extraction.

The apparatus of the present invention is directed to a surgical probe configured for insertion into the eye such that a distal end portion of the probe can be positioned between the iris and the lens capsule. The probe includes an electrical conductor configured to deliver energy outwardly therefrom. The probe further includes a non-conductive covering defining a port therethrough whereby energy from the electrical conductor can be emitted outwardly from the probe in a directionally controlled manner. The probe also includes an electrical connector for connecting the electrical conductor to an electrical energy source.

BRIEF DESCRIPTION OF THE DRAWINGS

For a more complete understanding of the present invention, reference may be had to the following Detailed Description read in connection with the accompanying drawings in which:

FIG. 7 is a second view of an eye undergoing treatment in accordance with the method of the present invention depicting the surgical device of the present invention in the eye.

DETAILED DESCRIPTION

Figure 1:
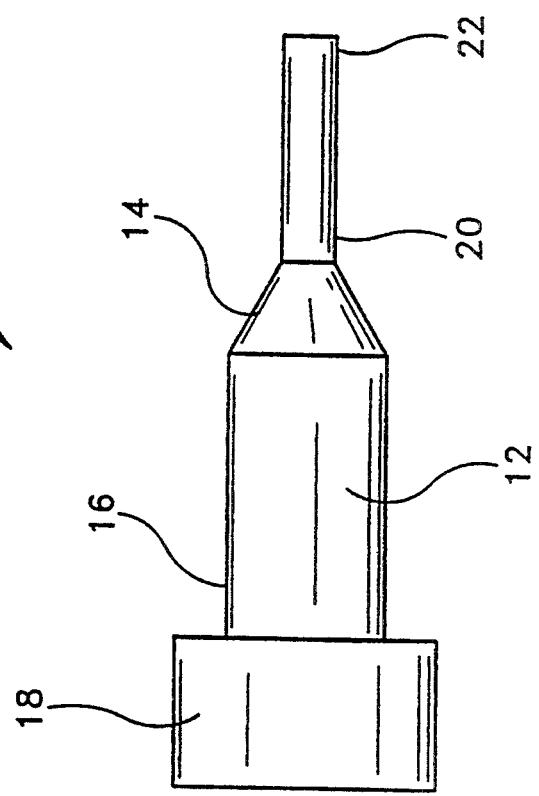
FIG. 1 is an elevational view of a surgical device constructed in accordance with a first embodiment of the device of the present invention.

A surgical probe constructed in accordance with the present invention is generally indicated at 10 of FIG. 1. Surgical probe 10 is constructed to be mounted on handpiece 12 at distal end portion 14 of handpiece 12. Proximal end portion 16 of handpiece 12 is configured to be attached to an energy source 18. Energy supplied by energy source 18 to handpiece 12 is directed from proximal end portion 16 to distal end portion 14. It will be appreciated that the manner in which energy is conducted through handpiece 12 will vary dependent upon the type of energy produced by source 18. For example, when probe 10 is configured to direct electrical energy to residual lens epithelial cells within the lens capsule, electrical energy from source 18 can be directed through handpiece 12 through the use of electrical wiring or through the use of other known electrical conductors. However, it is important that the energy be delivered to distal end portion 14 in a controlled manner in order to prevent the unwanted delivery of energy to the patient or to the surgeon using probe 10 of the present invention.

Probe 10 is dimensioned such that it can be inserted into the anterior chamber of the eye through an incision formed at the limbus in conjunction with the removal of a cataractous lens. Proximal end portion 20 of probe 10 is mounted on distal end portion 14 of handpiece 12. Proximal end portion 20 of probe 10 and distal end portion 14 of handpiece 12 are constructed such that energy directed through handpiece 12 is transmitted to probe 10. Probe 10 can be integrally formed on handpiece 12.

Figure 4:
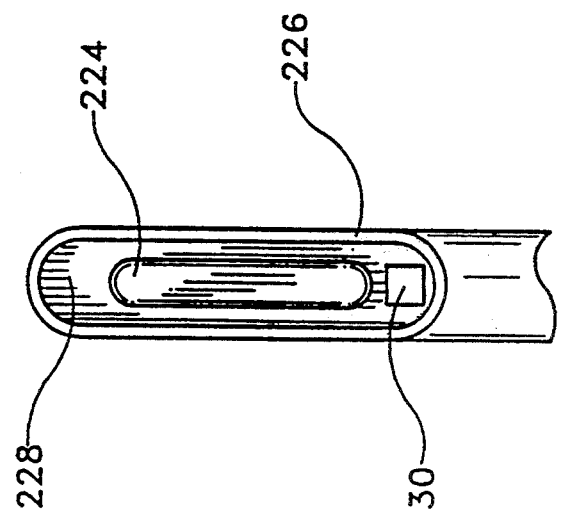
FIG. 4 is a bottom view of the probe of the second embodiment of the device of the present invention depicted in FIG. 3.
Figure 3:
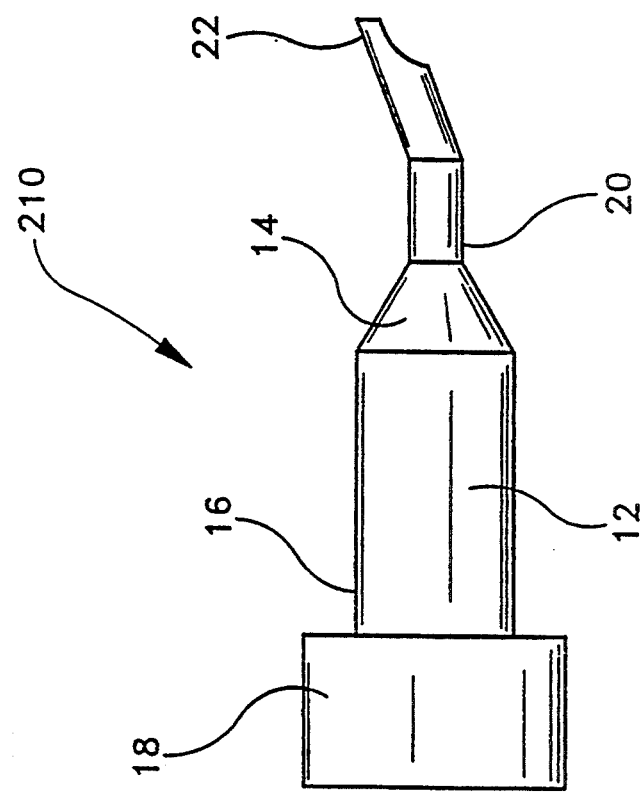
FIG. 3 is an elevational view of a second embodiment of a device constructed in accordance with the present invention.
Figure 5:
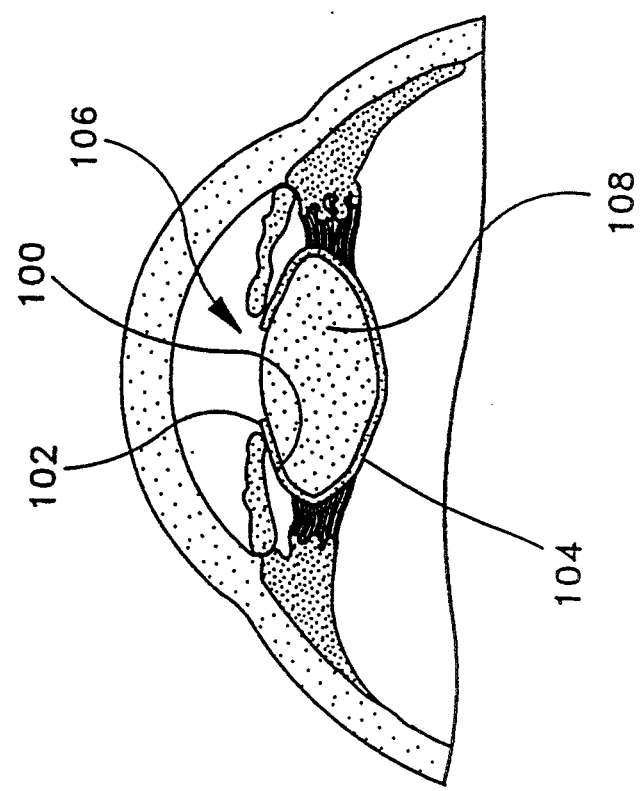
FIG. 5 is a view of an eye undergoing treatment in accordance with the method of the present invention.

Probe 10 further includes a distal end portion 22. In one embodiment of the present invention, distal end portion 22 is dimensioned and configured to be inserted into the lens capsule of the eye following extracapsular cataract extraction. The lens capsule is within the posterior chamber of the eye. Probe 10 can have a variety of configurations without departing from the spirit and scope of the present invention. For example, as depicted in FIG. 1, probe 10 can be straight and coaxially mounted on handpiece 12. However, it will be appreciated that it may be preferable to configure probe 10 such that it includes one or more bends along its length in order to enable a surgeon to reach otherwise difficult-to-reach areas of the lens capsule. This is particularly true when the target lens epithelial cells are located on interior surface 100 of anterior membrane 102 of lens capsule 104, as depicted in FIG. 5. The second embodiment of probe 210 depicted in FIGS. 3 and 4 is provided with a single bend in order to provide the surgeon with an enhanced ability to reach these difficult-to-reach areas of lens capsule 104. It will be appreciated that probe 10 can have a variety of other configurations having one or more bends for the purpose of facilitating the application of energy to lens capsule 104 without departing from the spirit and scope of the present invention.

Probe 10 is constructed to deliver energy along its length from proximal end portion 20 to distal end portion 22, and then to deliver such energy to interior surface 100 of lens capsule 104 for the purpose of destroying residual lens epithelial cells on interior surface 100. When probe 10 is configured to deliver electrical energy to interior surface 100 of lens capsule 104, it can include a single electrode, in which case electrical energy delivered by the electrode to interior surface 100 of lens capsule 104 travels outwardly from the electrode along the length of the electrode until it reaches a ground state. In this configuration of the present invention, electrical energy emanating from the single electrode of probe 10 will tend to destroy cells nearer to probe 10 where the electrical energy is at its greatest level.

Figure 2:
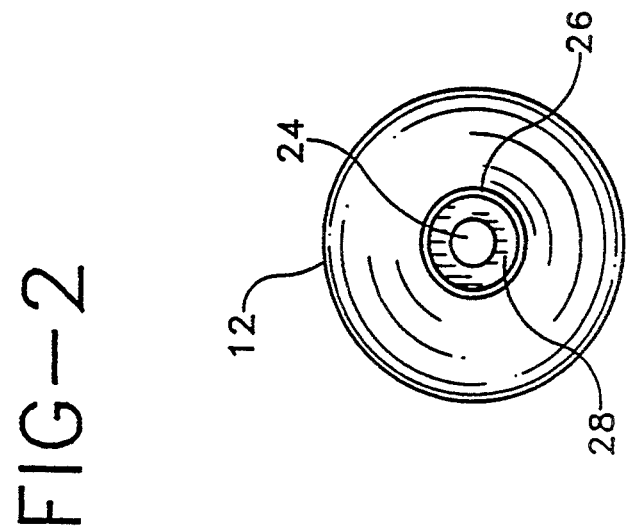
FIG. 2 is an end view of a surgical device constructed in accordance with a first embodiment of the device of the present invention.

In the embodiment of the present invention depicted in FIGS. 1 and 2, probe 10 includes first electrode 24 and second electrode 26 which are oriented such that electrical energy will tend to flow from one electrode to the other. Although first electrode 24 and second electrode 26 are depicted as being coaxial in FIGS. 1 and 2, it will be appreciated that the electrodes can be configured in various ways. For example, in the second embodiment of probe 210 depicted in FIGS. 3 and 4, first electrode 224 and second electrode 226 are not coaxially mounted. It is also to be appreciated that more than two electrodes can be used in conjunction with the device and method of the present invention.

In the embodiments of the present invention depicted in FIGS. 1–4, non-conducting zones 28, 228 separate first electrodes 24, 224 and second electrodes 26, 226. Thus, electrical current directed through one of the electrodes will enter the other electrode only after being transmitted through a medium other than non-conducting zones 28, 228. For example, electrical current directed through one electrode can be conducted by residual lens epithelial cells within lens capsule 104 in order to effect the destruction of such residual lens epithelial cells. In the alternative, electrical current can be transmitted through a conductor such as a balanced salt solution that can be introduced into the eye prior to application of power from energy source 18. This aspect of the present invention will be discussed in greater detail below in connection with the method of the present invention.

Figure 6:
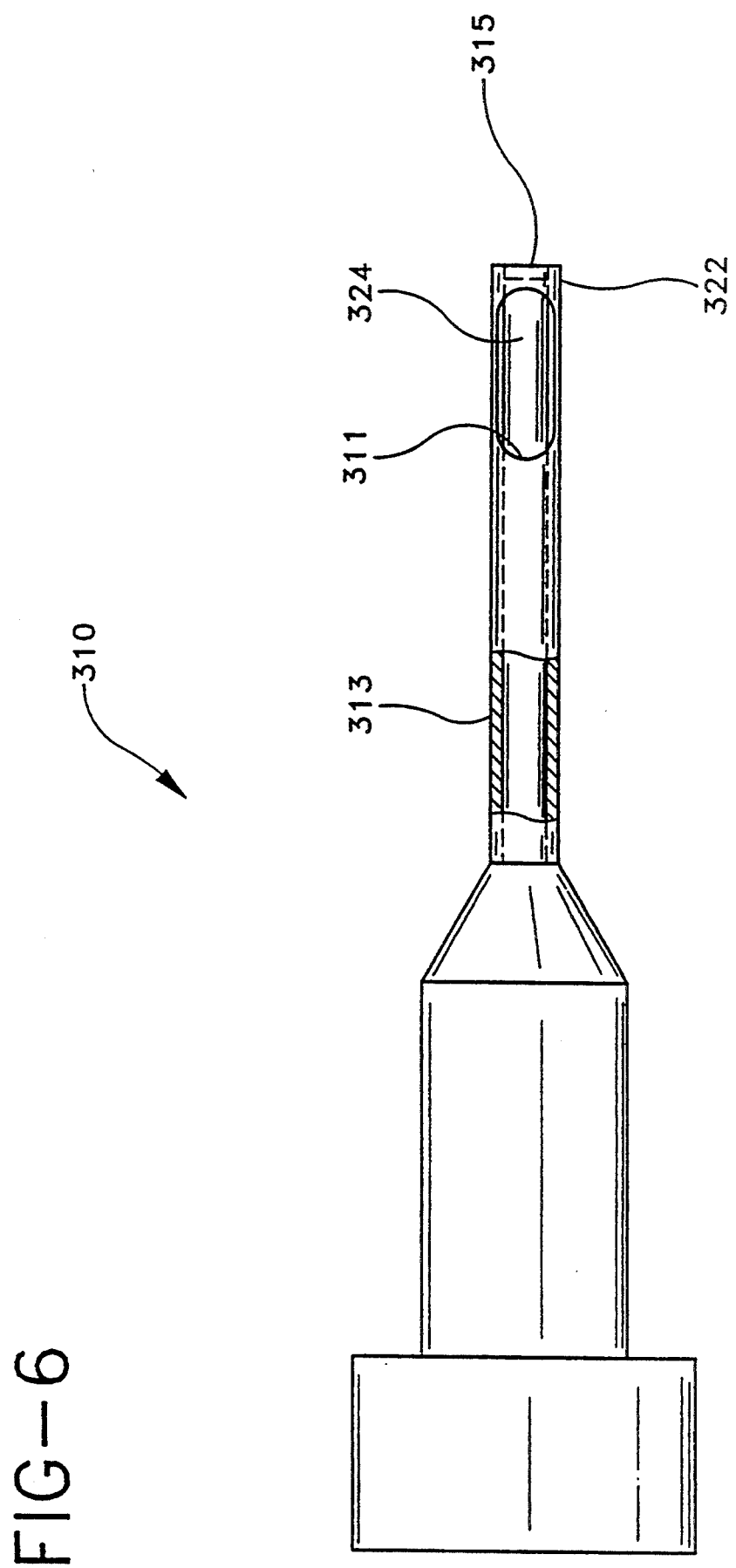
FIG. 6 is a partial cross-sectional view of a surgical device constructed in accordance with a third embodiment of the present invention.

In the embodiment of the invention depicted in FIG. 6, distal end portion 322 of probe 310 is configured such that the direction of emission of energy therefrom can be limited by a non-conductive cover 313 positioned about distal end portion 322 of probe 310. Non-conductive cover 313 can be formed from a variety of biocompatible, non-conductive materials, including, but not limited to, silicone. In this third embodiment, one or more portholes 311 are formed through non-conductive cover 313 proximal distal end portion 322 such that electrode 324 is exposed therethrough to an external environment of probe 310. It is believed to be preferable to form portholes 311 such that they are relatively close to tip 315 of probe 310, thereby minimizing the amount of probe 310 that must be inserted into the posterior chamber. Dependent upon the desired direction of emission of energy from probe 310, it may be desirable to insulate tip 315 of probe 310 in order to prevent energy from being emitted therefrom. It has been found in certain cases to be preferable to configure non-conductive cover 313 such that it covers tip 315 of probe 310, thereby preventing the emission of energy outwardly therefrom, when the embodiment of the present invention depicted in FIG. 6 is used to destroy residual lens epithelial cells from a position anterior to the lens capsule, as described in detail below with respect to the method of the present invention.

One of ordinary skill in the art will also recognize that it may be desirable to include a non-conductive cover in the first and second embodiments of the present invention depicted in FIGS. 1-4 in order to control the direction of emission of energy from probe 10, 210.

As above-discussed, non-conductive cover 313 can be constructed of silicone. It is preferable that the non-conductive cover 313 be secured to probe 10, 210, 310 such that it will not slide during use. It will be appreciated that movement of non-conductive cover 313 may cause damage to eye tissues. In addition, movement of non-conductive cover 313 may result in the unintended application of energy to ocular tissues other than the target tissues, thereby resulting in further ocular damage.

A desirable method for securing a silicone sleeve to a probe includes the step of providing a silicone sleeve having an internal diameter less than an external diameter of the distal end portion of the probe to which it is to be attached. The silicone sleeve is then immersed in ACS grade hexane until the sleeve has expanded sufficiently such that the sleeve can be placed over the distal end portion of the probe. Upon placement of the silicone sleeve over the distal end portion of the probe, the silicone sleeve is permitted to dry under a fume hood. As the silicone sleeve dries, it will tend to return to its original size, thereby securing itself to the probe. In the event that non-conductive covering 313 is to cover tip 315 of probe 310, a drop of silicone can be placed at tip 315 and allowed to dry. Alternatively, the sleeve can be a closed-ended sleeve, thereby obviating the need to apply a drop of silicone to tip 315. One or more portholes 311 can then be formed as desired through the non-conductive covering 313 using known cutting tools.

It will be appreciated that energy emitted from electrodes 24, 26 as depicted in FIGS. 1-4 will emanate outwardly from the tip of probe 10 in substantially all directions. In contrast, energy emitted from electrode 324 as depicted in FIG. 6 will be directed outwardly in a limited fashion. One of ordinary skill in the art will appreciate that energy will emanate from electrode 324 and through portholes 311 in a substantially conical pattern, such conical pattern having an axis lying substantially perpendicular to a longitudinal axis of probe 310. The direction of energy emitted from probe 310 can thus be controlled by selectively forming portholes 311 in probe 310. The direction of energy emitted from probe 310 can also be controlled by rotating probe 310 about its axis such that energy is emitted therefrom in the desired direction.

Energy source 18 can be any of a variety of sources of electrical or thermal energy. It has been found that electrical energy is preferable when used in conjunction with the device and method of the present invention due to the greater on/off capabilities associated with a source of electrical energy and due to the general availability of electrical energy sources in operating rooms. For example, most phacoemulsification systems have the capability of providing the requisite electrical power required by the device and method of the present invention. Energy source 18 can also be provided by a standard operating room system designed for bipolar cautery systems. The voltage and current limitations of such bipolar cautery systems have been shown to be safe and effective when used in conjunction with the device and method of the present invention. In addition, the alternating current produced by power supplies of this type tend to induce the oscillation of charged particles in balanced salt solutions, thereby resulting in a heating of the solution. The importance of this phenomenon will be discussed in greater detail below with respect to the method of the present invention. However, it is to be appreciated that the device and method of the present invention can also be used in conjunction with DC electrical power sources.

Distal end portion 22 of probe 10 is rounded in the embodiment depicted in FIGS. 1 and 2. The rounded configuration of distal end portion 22 facilitates the delivery of energy from electrodes 24, 26 to residual lens epithelial cells while simultaneously reducing the possibility of damaging lens capsule 104. However, various configurations of distal end portion 22 can be employed in conjunction with the present invention. For example, distal end portion 22 can be configured such that a plurality of electrodes can be extended therefrom when distal end portion 22 is disposed within lens capsule 104. The plurality of electrodes can be positioned relative to each other such that all or substantially all of interior surface 100 of lens capsule 104 can be subjected to energy at the same time using probe 10.

In another possible configuration, distal end portion 22 can include an inflatable tip which can be inflated when distal end portion 22 is in place within lens capsule 104. This embodiment can be used in connection with either electrical or thermal energy. When used in conjunction with electrical energy, the inflatable tip would preferably be constructed of a material having a capacity to conduct electricity such that electrical current could be passed therethrough in order to effect the destruction of residual lens epithelial cells on interior surface 100 of lens capsule 104. When the inflatable tip is used in connection with the application of thermal energy, it is preferably constructed of a heat conducting material such that heat generated within the inflatable tip is delivered to interior surface 100 and to the residual lens epithelial cells disposed thereon. Heating can be effected through a variety of known mechanisms, including the introduction of a heated fluid into the inflatable tip or through the application of energy from an energy source such as a laser to the contents of the inflatable tip.

Probe 10 can include temperature probe 30 disposed at distal end portion 22. Temperature probe 30 has a capacity to measure the temperature at distal end portion 22 and send a signal to deactivate energy source 18 when the temperature reaches a predetermined level, thereby preventing the possible application of excessive energy levels to the eye. Alternative mechanisms for preventing the application of excessive energy to the eye can also be utilized. For example, energy source 18 can be configured to provide energy pulses of relatively short duration, thereby reducing the likelihood that excessive energy will be delivered to the eye.

Probe 10 can also have an irrigation/aspiration capability whereby irrigating fluid can be introduced into the eye and tissue fragments and fluids can be removed from the eye during use of probe 10 in accordance with the method of the present invention.

The above-described device of the present invention is constructed for use in conjunction with the extracapsular extraction of a cataractous lens and the subsequent implantation of an artificial intraocular lens for the purpose of destroying residual lens epithelial cells prior to the implantation of the artificial intraocular lens. Extracapsular cataract extraction generally is performed by making an incision through the limbus of the eye in order to provide access to the anterior chamber of the eye. A surgical cutting tool is then inserted through the incision and into the anterior chamber. The surgical cutting tool is used to cut portion 106 from the anterior membrane 102 of lens capsule 104, thereby providing the surgeon direct access to lens 108 within lens capsule 104. Lens 108 is then removed through a known procedure such as phacoemulsification in which ultrasonic energy is imparted to lens 108 in order to break lens 108 into fragments which can then be aspirated from lens capsule 104 through the use of a phacoemulsification system having irrigation/aspiration capabilities.

In a first embodiment of the method of the present invention, a surgeon will employ the device of the present invention in order to remove any residual lens epithelial cells from lens capsule 104 following the removal of lens 108 from lens capsule 104. Probe 10 is inserted into the eye such that distal end portion 22 is positioned at a predetermined location within lens capsule 104. Probe 10 can be inserted through a newly formed incision, but preferably is inserted through the incision created in conjunction with the removal of the cataractous lens, thereby minimizing the trauma to the eye. Energy source 18 is then activated in order to provide energy to distal end portion 22 of probe 10. As discussed above, energy source 18 can be either an electrical energy source or a thermal energy source. However, in the preferred embodiment of the method of the present invention, electrical energy is used due to the above-discussed beneficial aspects of using such energy.

It will be appreciated that the energy directed to distal end portion 22 from energy source 18 will be transmitted into the tissues immediately surrounding distal end portion 22. Residual lens epithelial cells thus will tend to be destroyed by the application of energy from probe 10 due to their position on interior surface 100 of lens capsule 104. It has been found that the application of excessive energy to probe 10 will tend to damage lens capsule 104 itself. In particular, it has been discovered that distal end portion 22 of probe 10 will tend to stick to lens capsule 104 in the event that too much energy is directed to a single site on interior surface 100. The further delivery of energy from probe 10 to such a site on interior surface 100 will result in permanent, localized damage to lens capsule 104, including the possible perforation of lens capsule 104. For this reason, it is imperative that energy be supplied by probe 10 to lens capsule 104 in a controlled manner.

One technique for limiting the amount of energy delivered to a single site on interior surface 100 of lens capsule 104 is to move distal end portion 22 of probe 10 about lens capsule 104 rather than localizing the delivery of energy, thereby minimizing the possibility that too much energy will be delivered to a single site. In the event that this technique is used, it is preferable that probe 10 be moved about lens capsule 104 in a regimented or patterned manner in order to ensure that all areas of interior surface 100 are treated.

It has also been found that the use of balanced salt solutions such as interstitial fluids, osmotically balanced salt solutions, and viscoelastic solutions, can minimize the possibility of probe 10 sticking to interior surface 100 of lens capsule 104 if such solutions are placed in lens capsule 104 prior to the application of power to probe 10. Balanced salt solutions are commonly used in ophthalmic procedures such as extracapsular cataract extraction for the purpose of preventing the collapse of the anterior chamber due to the loss of fluid through the incision. Such balanced salt solutions not only provide a buffer between probe 10 and interior surface 100, but also provide a conducting medium through which electrical energy from probe 10 can pass, thereby facilitating the transfer of energy from probe 10 to the residual lens epithelial cells.

Particularly beneficial results have been achieved through the use of viscoelastic solutions containing 2-hydroxypropylmethyl cellulose, such as the solutions sold by Storz Instrument Company, a wholly-owned subsidiary of the assignee of this invention, under the trademarks "OCCUCOAT" and "OCCUCOAT PF". It has been discovered that probe 10 is less likely to stick to interior surface 100 of lens capsule 104 at a given power setting when "OCCUCOAT" viscoelastic solutions are used as compared to other balanced salt solutions or water. This benefit may be the result of the fact that the application of electrical energy from probe 10 to interior surface 100 in the presence of "OCCUCOAT" viscoelastic solution causes the viscoelastic solution to form a precipitate or gel which acts as a barrier between probe 10 and interior surface 100. The resulting precipitate or gel dissipates a few seconds after terminating the application of electrical energy and therefore does not pose any complications in the surgical procedure. In addition, the size and duration of this precipitate or gel has been found to be reproducible and proportional to the intensity of the power and the duration of application of power from probe 10. This predictable change in the physical characteristics and appearance of the "OCCUCOAT" viscoelastic material thus enables a surgeon to identify the areas that have been treated with energy from probe 10 for the purpose of destroying residual lens epithelial cells.

In addition to the above-described benefits, it has also been discovered that the use of a viscoelastic solution containing 2-hydroxypropylmethyl cellulose, such as "OCCUCOAT" viscoelastic material, in conjunction with the method of the present invention results in significantly greater temperature increases when compared to other balanced salt solutions and water. Alternating current produced by energy source 18 causes the oscillation of the charged particles in a viscoelastic solution containing 2-hydroxypropylmethyl cellulose, thereby resulting in the heating of the viscoelastic solution. The maximum temperature achieved using "OCCUCOAT" viscoelastic solution used in conjunction with the method of the present invention is 100° C. Such heat serves to destroy residual lens epithelial cells within the lens capsule. It is believed that the oscillation of charged particles within the viscoelastic solution caused by the application of AC current thereto, as well as the local osmotic differences resulting from such oscillations, further facilitates the destruction of the lens epithelial cells within the lens capsule.

It has been found that energy emitted from probe 10 in conjunction with the method and device of the present invention may reach the iris, thereby causing tissue damage to the iris. For this reason, it may be desirable to provide an iris shield that can be placed between the lens capsule and the iris prior to directing energy through probe 10. In one embodiment of the method of the present invention, an iris shield formed from a hydrogel material is placed between the iris and the lens capsule in order to prevent energy from probe 10 from adversely affecting the iris. One of ordinary skill in the art will recognize that other materials can be used to form an iris shield in accordance with the teachings of the present invention, so long as such material is biocompatible, is capable of shielding the iris from energy emitted from probe 10, and is not structurally compromised by energy emitted from probe 10.

It will be appreciated that the amount of energy required to perform the method of the present invention will vary dependent upon a number of factors, including the size and configuration of the electrode(s) of probe 10 and the presence or absence of a conducting medium within lens capsule 104. Devices with larger electrode surface areas will have higher power requirements. In addition, the desirable power level will vary dependent upon each surgeon's chosen technique. For example, if probe 10 is used in a relatively quick, sweeping motion within lens capsule 104, a higher power may be used due to the fact that there will be less power delivered to any single site on interior surface 100 of lens capsule 104. Similarly, greater power levels can be used when a viscoelastic solution containing 2-hydroxypropylmethyl cellulose is present due to the above-referenced characteristics of such viscoelastic solutions. However, if the surgeon prefers to treat individual sites on a methodical or sequential basis, it may be desirable to utilize lower power levels in order to minimize the possibility of damage to lens capsule 104.

In some cases it may be preferable to utilize two or more different configurations of probe 10 in conjunction with the method of the present invention in order to ensure that all areas of interior surface 100 are subjected to the energy emanating from probe 10. For example, probe 210 may be inserted for use following use of probe 10 in order to ensure that areas of interior surface 100 that may not have been treated using probe 10 are subjected to energy from probe 210. It may also be necessary in certain cases to form a second incision through the limbus in order to provide a different angle of attack for probe 10, thereby ensuring that all areas of interior surface 100 are subjected to the energy emanating from probe 10.

Following the application of energy to lens capsule 104 and the resulting destruction of residual lens epithelial cells, the surgeon deactivates and removes probe 10 from the eye. Upon the removal of particulate matter and any balanced salt solutions from lens capsule 104 using known irrigation/aspiration techniques, the surgeon can proceed with the implantation of an artificial intraocular lens 104 using a variety of known methods.

In a second embodiment of the method of the present invention, a probe 310 capable of emitting energy from its distal end portion in a predetermined direction is provided. Although probes of various configurations can be used, it has been found to be advantageous to employ a probe such as that depicted in FIG. 6 and disclosed in detail herein in order to control the emission of energy from the probe. It is to be appreciated that the second embodiment of the method of the present invention can be used either before or after the extracapsular extraction of the cataractous lens. In the second embodiment of the method of the present invention, distal end portion 322 is inserted into the eye such that it is positioned within the posterior chamber of the eye between the iris 101 and the anterior membrane 102 of lens capsule 104 and such that porthole 311 is directed posteriorly towards the lens capsule. Energy is then directed to probe 310 such that energy is emitted therefrom at a level sufficient to destroy residual lens epithelial cells on lens capsule 104. It will be appreciated that energy emanating from probe 310 will pass through lens capsule 104 and destroy residual lens epithelial cells disposed on interior surface 100 thereof. Dependent upon the configuration of probe 310, it may be necessary to move probe 310 about in order to ensure that energy is directed to all portions of lens capsule 104, thereby ensuring that as many residual lens epithelial cells as possible are destroyed. The delivery of energy to probe 310 is then ceased and the probe is withdrawn from the eye. It is to be appreciated that a second probe having a different configuration can be inserted as above-discussed in order to reach portions of lens capsule 104 not reachable using probe 310. A second probe also can be inserted through a second incision formed at the limbus as above-discussed in order to reach portions of lens capsule 104 not reachable using probe 310. Furthermore, balanced salt solutions such as interstitial fluids, osmotically balanced salt solutions, and viscoelastic solutions, as above-discussed, can be used in connection with the second embodiment of the method of the present invention.

Although the device and method of the present invention have been disclosed herein with respect to certain preferred embodiments, it will be apparent to one of ordinary skill in the art that various modifications can be made to the invention without departing from the spirit and scope of the invention disclosed and claimed herein.

What is claimed is:

1. A method for destroying residual lens epithelial cells in a lens capsule of an eye, said method comprising the steps of:
   providing an iris shield constructed of a material capable of preventing the transmission energy therethrough at levels potentially harmful to an iris of said eye;
   placing said iris shield between said lens capsule and said iris;
   providing a probe having a distal end portion configured for insertion into an eye, said probe having a capacity to emit energy outwardly from said distal end portion;
   inserting said first probe into a posterior chamber of said eye;
   delivering energy to said distal end portion of said first probe such that energy is emitted outwardly from said distal end portion of said first probe at a level sufficient to destroy residual lens epithelial cells on said lens capsule;
   ceasing the emission of energy from said distal end portion of said first probe;
   removing said first probe from said eye; and
   removing said iris shield from said eye.

2. A method for destroying residual lens epithelial cells in a lens capsule of an eye in accordance with claim 1, wherein said distal end portion of said probe is inserted into said lens capsule.

3. A method for destroying residual lens epithelial cells in a lens capsule of an eye in accordance with claim 1, wherein said distal end portion of said probe is inserted between said lens capsule and said iris.

4. A method for destroying residual lens epithelial cells within a lens capsule of an eye, said method comprising the steps of:
   providing a first probe having a distal end portion configured for insertion into an eye, said first probe having a capacity to emit energy outwardly from said distal end portion;
   inserting said first probe into said eye such that said distal end portion of said probe is positioned between an iris of said eye and said lens capsule;
   delivering energy to said distal end portion of said first probe such that energy is emitted outwardly from said distal end portion of said first probe at a level sufficient to destroy residual lens epithelial cells on said lens capsule;
   ceasing the emission of energy from said distal end portion of said first probe; and
   removing said first probe from said eye.

5. A method for destroying residual lens epithelial cells in a lens capsule of an eye in accordance with claim 4, wherein said first probe comprises an electrode surrounded by a non-conductive cover, said non-conductive cover defining a porthole therethrough whereby energy can be emitted outwardly from said electrode through said porthole defined through said non-conductive cover.

6. A method for destroying residual lens epithelial cells in a lens capsule of an eye in accordance with claim 5, wherein said method further comprises placing said probe in said eye such that said porthole is directed posteriorly, whereby energy emitted from said probe is directed posteriorly toward said lens capsule.

7. A method for destroying residual lens epithelial cells in a lens capsule of an eye in accordance with claim 4, wherein said method further comprises:
   providing an iris shield constructed of a material having a capacity to prevent energy emitted from said probe from damaging said iris;
   placing said iris shield between said iris and said lens capsule prior to delivering energy to said distal end portion of said probe; and
   removing said iris shield from said eye after ceasing the delivery of energy from said distal end portion of said probe.

8. A method for destroying residual lens epithelial cells in a lens capsule of an eye in accordance with claim 4, wherein said method further comprises moving said distal end portion of said probe within said eye as energy is emitted from said distal end portion such that energy is delivered to a plurality of preselected areas of said lens capsule.

9. A method for destroying residual lens epithelial cells in a lens capsule of an eye in accordance with claim 4, wherein said method further comprises the steps of:
   providing a second probe having a distal end portion configured for insertion into said eye, said second probe having a capacity to emit energy outwardly from its distal end portion, said second probe having a configuration different from a configuration of said first probe, whereby said second probe can be used to direct energy to areas of said lens capsule not reachable using said first probe;
   inserting said second probe into said eye after removal of said first probe from said eye such that said distal end portion of said second probe is positioned between said iris of said eye and said lens capsule;
   delivering energy to said distal end portion of said second probe such that energy is emitted outwardly from said distal end portion of said second probe at a level sufficient to destroy residual lens epithelial cells on said lens capsule;
   ceasing the emission of energy from said distal end portion of said second probe; and
   removing said second probe from said eye.

10. A method for destroying residual lens epithelial cells in a lens capsule of an eye in accordance with claim 4, wherein said energy delivered to said distal end portion of said first probe is electrical energy.

11. A method for destroying residual lens epithelial cells in a lens capsule of an eye in accordance with claim 4, wherein said energy delivered to said distal end portion of said first probe is thermal energy.

12. A method for destroying residual lens epithelial cells in a lens capsule of an eye in accordance with claim 4, wherein said first probe is inserted through a first incision at the limbus of said eye, and wherein said method further comprises the steps of:
   forming a second incision at the limbus of said eye, said second incision being spaced from said first incision;
   providing a second probe having a distal end portion configured for insertion into said eye, said second probe having a capacity to emit energy outwardly from its distal end portion, said second probe having a configuration different from a configuration of said first probe whereby said second probe can be used to direct energy to areas of said lens capsule not reachable using said first probe;
   inserting said second probe into said eye through said second incision at the limbus of said eye;
   delivering energy to said distal end portion of said second probe such that energy is emitted outwardly from said distal end portion of said second probe at a level sufficient to destroy residual lens epithelial cells on said lens capsule;

ceasing the emission of energy from said distal end portion of said second probe; and removing said second probe from said eye.

13. A method for destroying residual lens epithelial cells in a lens capsule of an eye in accordance with claim 4, wherein said probe is inserted into said eye after an extracapsular cataract extraction.

14. A method for destroying residual lens epithelial cells in a lens capsule of an eye in accordance with claim 4, wherein said method further comprises extracting a cataractous lens from said lens capsule following removal of said probe from said eye, wherein said cataractous lens is removed utilizing an extracapsular cataract extraction procedure.

* * * * *